: US010422457B2

United States Patent
Singer et al.

(10) Patent No.: US 10,422,457 B2
(45) Date of Patent: Sep. 24, 2019

(54) SWIVEL KNUCKLE CONNECTION

(71) Applicant: Medtronic Xomed, Inc., Jacksonville, FL (US)

(72) Inventors: Scott Andrew Singer, Watauga, TX (US); Ken Riedel, Weatherford, TX (US); Juan P. Angulo, Fort Worth, TX (US)

(73) Assignee: Medtronic Xomed, Inc., Jacksonville, FL (US)

( * ) Notice: Subject to any disclaimer, the term of this patent is extended or adjusted under 35 U.S.C. 154(b) by 456 days.

(21) Appl. No.: 15/098,477

(22) Filed: Apr. 14, 2016

(65) Prior Publication Data

US 2017/0299101 A1  Oct. 19, 2017

(51) Int. Cl.
| | | |
|---|---|---|
| *F16L 27/08* | (2006.01) | |
| *F16L 39/04* | (2006.01) | |
| *A61B 17/00* | (2006.01) | |

(52) U.S. Cl.
CPC ....... *F16L 27/0841* (2013.01); *F16L 27/0828* (2013.01); *F16L 39/04* (2013.01); *A61B 2017/00477* (2013.01); *Y10T 29/49826* (2015.01)

(58) Field of Classification Search
CPC ............... F16L 27/0824; F16L 27/0828; F16L 27/0841; F16L 27/0845; F16L 27/0849; F16L 39/04; A61B 2017/00477; Y10T 29/49826
USPC ...................................... 285/276, 121.6, 281
See application file for complete search history.

(56) References Cited

U.S. PATENT DOCUMENTS

| | | | |
|---|---|---|---|
| 2,155,640 | A | 4/1939 | Bruce |
| 2,726,104 | A | 12/1955 | Boitnott et al. |
| 4,203,222 | A | 5/1980 | Mattchen |
| 4,614,498 | A | 9/1986 | Vaccaro |
| 4,804,206 | A * | 2/1989 | Wood .................. F16L 27/0841 285/276 X |
| 5,179,976 | A | 1/1993 | Boland et al. |
| 6,550,817 | B1 * | 4/2003 | Mitchell ............. F16L 27/0828 285/276 X |
| 2005/0140138 | A1 * | 6/2005 | Byerly |
| 2006/0142656 | A1 | 6/2006 | Malackowski et al. |
| 2016/0003387 | A1 | 1/2016 | Taguchi et al. |
| 2017/0016559 | A1 * | 1/2017 | Chung ................ F16L 27/0828 |

FOREIGN PATENT DOCUMENTS

| | | |
|---|---|---|
| GB | 464768 A | 5/1938 |
| WO | WO-2015183164 A1 | 12/2015 |

OTHER PUBLICATIONS

Invitation to Pay Additional Fees dated Jun. 23, 2017 in corresponding International Application No. PCT/US2017/027162.
International Search Report and Written Opinion dated Aug. 31, 2017 in corresponding International Application No. PCT/US2017/027162.

(Continued)

*Primary Examiner* — Greg Binda
*Assistant Examiner* — Zachary T Dragicevich
(74) *Attorney, Agent, or Firm* — Harness Dickey & Pierce (57) ABSTRACT

A swivel knuckle assembly for interconnecting a motor and a supply line. The knuckle assembly may include a bearing member to reduce a coefficient of friction. A locking mechanism is disclosed to connect members of the knuckle assembly.

16 Claims, 7 Drawing Sheets

(56) References Cited

OTHER PUBLICATIONS

"Medtronic Midas Rex® MR7 Next Generation of High-Speed Pneumatic Motors"; Brochure, 4 pages, 2010.
International Preliminary Report on Patentability dated Oct. 25, 2018 in corresponding/related International Application No. PCT/US2017/027162.
Office Action dated Apr. 2, 2019 in corresponding/related European Application No. 18210241.8.

\* cited by examiner

SWIVEL KNUCKLE CONNECTION

CROSS-REFERENCE

This application is being filed concurrently with U.S. patent application Ser. No. 15/098,491 filed on Apr. 14, 2016.

FIELD

The disclosure is directed to a connection assembly, and particularly to a swivel mounting connection mechanism between a power supply and a motor.

BACKGROUND

This section provides background information related to the present disclosure which is not necessarily prior art.

In various operations, such as in surgical operations, repair operations, and other operations or procedures, a motor may be supplied with power. The power supply may include a fluid power supply, such as a pneumatic power drill. The fluid may flow from a power source through tubing to the motor and then though a return path to the source or to an exhaust. During operation, it may be desired to move the tool to a selected configuration relative to the power supply and the tubing. A knuckle mechanism similar to that used in the Midas Rex® MR7 Touch Motor, sold by Medtronic, Inc. having a place of business in Minnesota, may be used to allow for twisting movement of the drill motor relative to the supply tubing.

SUMMARY

This section provides a general summary of the disclosure, and is not a comprehensive disclosure of its full scope or all of its features.

A knuckle assembly for a motor may include a swivel interconnection between a supply line, including a tube, and a motor body or housing. The knuckle may include a first portion that connects to the supply tube and a second portion that connects to the motor housing. The first and second portions may rotate relative to one another. The rotation may be substantially 360° or a limited portion of a full 360° rotation around or relative to one of the portions. Therefore, the knuckle assembly can allow rotation of the motor housing relative to the supply line during use. The knuckle, therefore, also includes a sealed connection that allows rotational movement of the motor housing relative to the supply line.

The knuckle assembly may further include a connection mechanism that locks and seals a connection of the first portion and the second portion while allowing rotational movement between the two portions. The connection may include one or more members that may be positioned during assembly to allow the knuckle to rotate. Selected sealing members may also be provided to seal the connection of the supply line and tubing to the motor housing. Therefore, a fluid supply from the power source will not escape prior to or during operating or powering the motor in the motor housing.

The swivel portion includes the bearing members that are solid or a one-piece bearing member. The bearing member may be, therefore, a mono-piece, such as one formed in a single piece mold. The bearing member may be mono-piece annular member. More than one of the annular bearing may be positioned in the knuckle, however. The bearing member may have a coefficient of friction relative to other materials in the knuckle to reduce friction during movement and contact between the two portions of the knuckle assembly. The knuckle connection assembly can further include sealing members that may not substantially interfere with the swivel of the knuckle, such as increasing a coefficient of friction between the two portions of the knuckle assembly during operation.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figures 1, 2B:
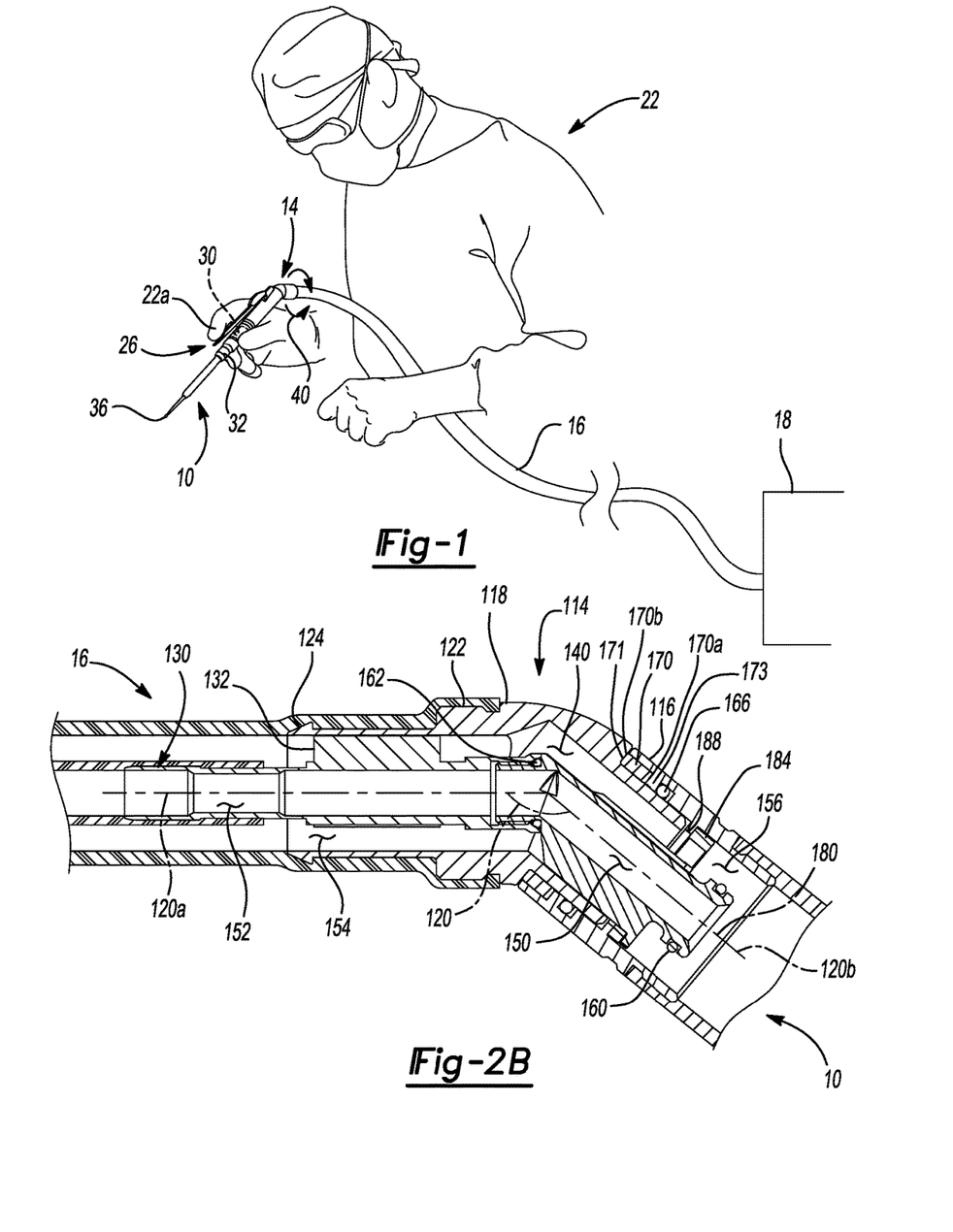
FIG. 1 is a schematic exemplary environmental view of a drill motor.
FIG. 2B is a cross sectional view of a swivel knuckle assembly taken along line 2B of FIG. 2A.

With initial reference to FIG. 1, a motor assembly 10 may connect to a knuckle connection assembly 14 that interconnects the motor assembly 10 and a supply line 16 (which may also be referred to as a supply). The supply line 16 may be a hose forming a passage or more than one passage therethrough. For example, concentric passages may be formed through the supply line 16, as discussed herein. The supply line 16 is connected to a power supply 18, such as a pneumatic or fluid power supply. The power supply 18 can provide a fluid through the supply line 16 in the knuckle 14 to the motor housing assembly 10.

The knuckle assembly 14, as discussed herein, may form an angle extending relative to the motor assembly 10. It is understood that various portions of the knuckle assembly 14 need not be limited to an angled connection. As discussed herein a bearing or connection mechanism may be used with a straight connection as well. Further, although a surgical drill motor assembly is illustrated as the motor assembly 10, the motor assembly 10 need not be limited to a surgical drill motor.

A user 22 may operate the motor assembly 10. For example, the user 22 may actuate a switch 26 that is interconnected with the motor assembly 10 to power on and off a drill motor 30 that is within a housing 32 of the motor assembly 10. Powering the motor 30 via the switch 26 may operate, such as to rotate, a tool 36. The tool 36 may be in an appropriate tool such as a mill. It is understood that other tools may also be operated with the motor 30, such as a reamer, a cutting instrument, a rotating cutting instrument, or other appropriate tool. It may be further understood that the tool 36 need not be a surgical tool but can be a tool used for any appropriate procedure or operation. For example, the tool 36 may include a tap for forming threads in a material, such as a support beam for a motor vehicle. Further, the tool 36 may be a drill bit that is used to form a hole or passage in a bulkhead of a watercraft. Therefore, it is understood that the subject disclosure is not limited only to a surgical procedure or instrument, but that the motor assembly 10 may be used in an appropriate procedure and the disclosed surgical procedure is merely exemplary.

Regardless of the use of the motor assembly 10, the housing 32 allows the user 22 to grasp the motor assembly 10 with a single hand 22a of the user 22 or more than the single hand of the user 22. Further, the switch 26 may be operated with one or more digits of the user 22 during a procedure. Moreover, during a procedure, the knuckle assembly 14 allows the housing 32 including the motor assembly housing 10 and the tool 36 to be rotated relative to the supply line 36 without twisting or rotating the supply line 16. Accordingly, the motor housing 10 may rotate substantially 360° as indicated by the double-headed arrow 40 without twisting or rotating the supply line 16. The rotation of the assembly 10, however, is not required to be 360° and may be less and/or multiple movements over the same portion of movement. As discussed further herein, the supply of fluid through the knuckle assembly 14, however, may be substantially sealed and the rotation may be assisted with one or more bearing members within the knuckle assembly to achieve a selected coefficient of friction and smoothness of rotation in the direction of the double-headed arrow 40. It is further understood that the drill motor housing 10 may be rotated in either direction (i.e. clockwise or counterclockwise) back and forth or may be only rotated in a single direction while the sealing is maintained with the knuckle assembly 10.

Figure 2A:
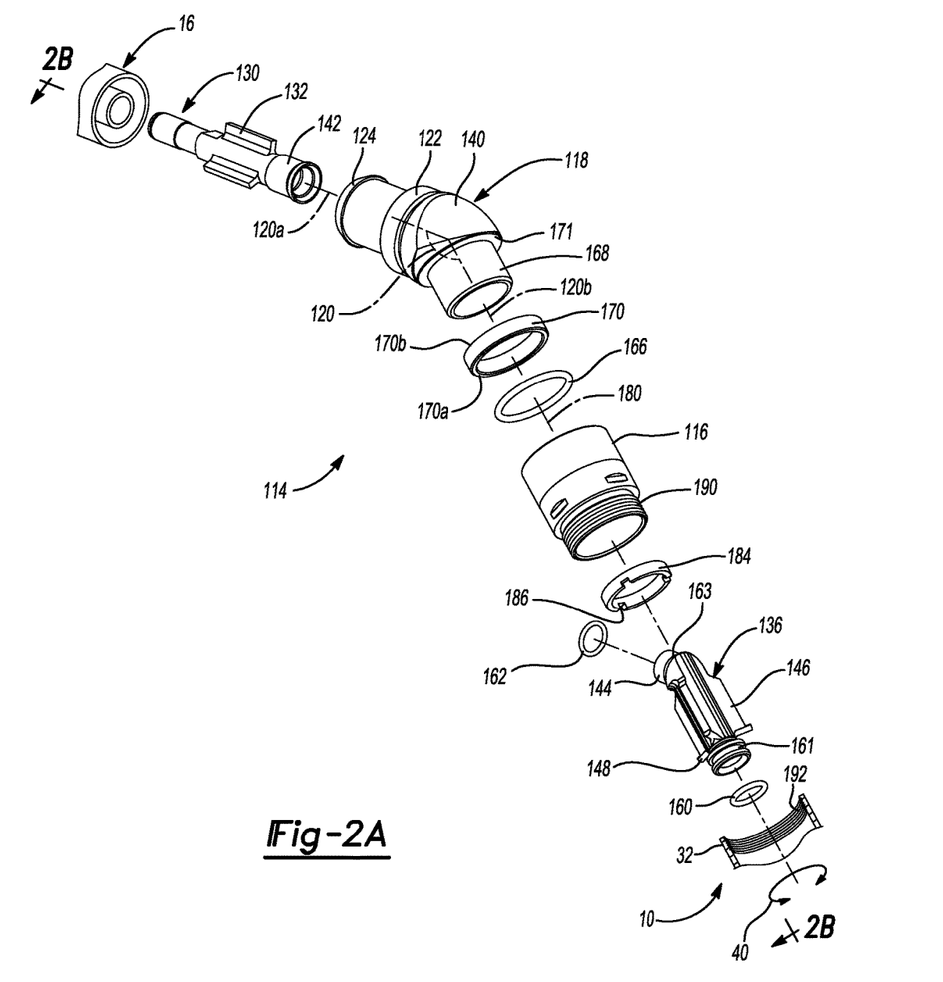
FIG. 2A is an exploded view of a knuckle assembly according to various embodiments.

With reference to FIGS. 2A and 2B, the knuckle assembly 14 is illustrated in a first embodiment knuckle assembly 114. The knuckle assembly 114 may include two portions including a first connection portion 116 configured to connect to the motor assembly 10 and a second angle or housing connection portion 118 configured to connect to the supply line 16. The two portions 116 and 118 can both be angled or have any selected angle. For example, the angled portion 118 can include an angle 120 of about 10° to about 60°, including about 40° between a first axis 120a and a second axis 120b. The angle 120 is be angled between the two axis lines 120a, 120b extending through substantially straight portions of the angled portion 118. It is understood, however, that the first portion 116 may also include an angle or may include the entire angle for the knuckle assembly 114. As illustrated in FIGS. 2A and 2B, however, the knuckle 114 may include the second portion 118 that includes the angle 120.

The second portion 118 may include a connection mechanism to connect with the supply line 16, such as a threaded portion 122. A barbed or ramped portion 124 may also assist in forming a connection between the supply 16 and the second portion 118. The knuckle assembly 114 may further include a barb member 130 that allows for a high pressure to pass through the knuckle 114 to the motor assembly 10. The barb 130 may include radially extending alignment fins 132 extending from an outer surface of the barb 130. The barb 130 may further include engaging features, such as one or more radial protrusions, to engage and assist in connection and fixation to the supply line 16. At an end opposite the connection to the supply line 16, the barb 130 may connect with a nozzle insert 136 within the knuckle assembly 114, generally near an angled region 140 (generally defining the angle 120) of the second portion 118. A proximal connector 142 of the barb can receive internally a distal connector portion 144 of the nozzle 136 and be held in place with various connecting mechanisms such as threads, welding, or other connecting assemblies. The nozzle 136 may also include radially extending stabilizing or directing fins 146 that may terminate or include extending fingers or tabs 148.

The fins 132 of the barb 130 can engage an internal surface of the second portion 118 and the fins 146 of the nozzle 136 can engage an internal surface of at least the first portion 116. The internal surfaces of the first portion 116 and the second portion 118 may be cylindrical wall surfaces. Further, the fins 132 and the fins 146 may both engage only or substantially only the internal wall of the second portion 116. Therefore, the barb 130 and the nozzle 136 can be substantially radially stabilized within the knuckle 114 by the respective fins 132, 136 extending to engage the internal surfaces of the portions 116, 118. Further, the connection of the barb 130 to the nozzle 144 can assist in maintaining a connection and axial fixation of the knuckle assembly 114.

As discussed above, the supply line 16 can connect with the knuckle 114 to allow for delivery of a drive fluid to the motor assembly 10. The high pressure or drive line or flow path can extend through an internal passage 150 of the nozzle and an internal passage 152 of the barb 130. The pressure in the high pressure path may be about 60 psi to about 180 psi relative to a vacuum or an absolute pressure. Between an internal wall and an external wall of the barb 130 may be an exhaust passage 154 which can extend to an exhaust passage 156 between the nozzle 136 and an internal wall of the first portion 116. The exhaust passage may contain a pressure lower than the high pressure flow path. Further, the exhaust passage 154, 156 may be concentric over the internal passages 150, 152.

Sealing the fluid passages 150, 152, 154, 156 can be at least a first O-ring 160 that may extend around a distal end 161 of the nozzle 136 and a second O-ring 162 that may extend around a proximal end 163O of the nozzle 136. The first O-ring 160 can assist in sealing the assembly 10 to the nozzle 136 and the second O-ring 162 can assist in sealing the nozzle 136 to the barb 130. It is understood that other appropriate O-rings or sealing members may be provided and remain within the scope of the subject disclosure and the appended claims.

A further sealing member, such as a third O-ring 166, can seal, at least to the exhaust, between the first member 116 and the second portion 118. The third O-ring 166 may be provided between an external wall 168 of a connection portion of the second member 118 and an internal wall of the first portion 116. A first swivel bearing 170 may also be provided between the external wall 168 of the second portion 118 and the internal wall of the first portion 116. The first swivel bearing has a first end surface 170a and a second end surface 170b. The first swivel bearing 170 also bears between a first transverse extending wall surface 171 and a second transverse wall 173 on the first end surface 170a and the second end surface 170b. The first swivel bearing 170 may bear on the end surfaces 170a, 170b due to an axial loading on the knuckle 114 along the axis 120b, 180 due, at least in part, to puling, pushing, and/or other movement of the assembly 10 relative to the supply line 16 and/or the supply 18. The first transverse extending wall surface 171 is extending from an external surface of the second portion 118 generally transverse to the axis 120b. The second transverse wall 173 extends internally from the first portion 116 and generally transverse to the axis 120b.

As illustrated in the assembled view in FIG. 2A, the swivel bearing 170 can assist in bearing or reducing direct contact between the first portion 116 and the second portion 118. According to various embodiments, the first portion and the second portion 118 of the knuckle assembly 114 may be formed of a selected metallic material such as stainless steel, titanium, or other appropriate metallic materials. The bearing member 170 may include a non-metallic material or be formed entirely of a non-metallic material such as a polyethylene, polyetheretherketo one (PEEK), or other appropriate non-metallic materials. Further examples of materials performing the swivel bearing 170 can include polytetrafluoroethylene (PTFE) including Teflon® PTFE. It is understood, however, that other materials may be used to form the swivel bearing 170. The bearing 170 may be selectively formed of materials having an appropriate coefficient of friction, rigidity, and ability to be sterilized. For example, if the bearing is made of PEEK or PTFE the bearing may be heat or steam sterilized for several cycles.

The knuckle assembly 170 may be held axially, such as generally along an axis 180 extending between the first member 116 and the second portion 118 during use and operation of the knuckle 114 due to the connection between the barb 130 and the nozzle 136. As discussed above, the nozzle 136 may be fixed to the barb 130 according to selected fixation mechanisms including threads, welding, and the like. The nozzle 136 includes the fingers or tabs 148 that may engage a second swivel bearing 184. For example, the second swivel bearing may include a number of indents 186 that is at least equal to the number of tabs 148 of the nozzle 136. Therefore, the second swivel bearing 184 may be held rotationally fixed relative to the nozzle 136. The second bearing member 184 may engage an internal wall or surface 188 of the first portion 116 of the knuckle 114. The internal wall 188 may extend generally transverse to the axis 120b. The knuckle 114, therefore, may be axially connected due to the connection of the barb 130 with the nozzle 136 and the nozzle 136 with the bearing 184 engaging the wall 188.

Rotation or movement of the first portion 116 may occur, therefore, relative to the second portion 118 due to the positioning of the bearing members 170 and 184. The first member 116 may further include an external thread 190 to engage an internal thread 192 of the motor housing 32 of the motor assembly 10. Therefore, the motor housing 32 is connected directly to the first member 116 and further the motor is connected to the nozzle 136 through internal passages to allow for the supply fluid to power the motor 30 within the assembly 10. Accordingly, rotation of the motor assembly 10 generally in the direction of the double-headed arrow 40 will allow for rotation of the first portion 116 due, at least in part, to the second bearing member 184 and the first bearing 170 relative to the second portion 118. The bearings 170, 184 may bear and engage the moving portions on end surfaces and outer and inner surfaces as the portions move relative to one another. Accordingly, the knuckle 114 may allow swiveling the rotation of the motor assembly 10 relative to the supply line 16 without twisting or rotating the supply line 16 due to rotation of the motor assembly 10.

During rotation and/or other movement the angle 120 of the knuckle 114 may be fixed and maintained. Thus, the orientation of the assembly 10 may change, but the angle 120 may not change.

Both of the bearing members 170, 184 may be formed of the materials, as discussed above. Further, the bearings may be formed by a molding process, including injection, extrusion, or other appropriate molding process. The bearing members 170, 184, therefore, may be formed as one piece or mono-piece bearing members. The bearing members 170, 184 are then configured to be assembled in a single assembly operation by placement (e.g. sliding or expanding and sliding) of the respective bearing member 170, 184 in its assembled location.

Figure 3A:
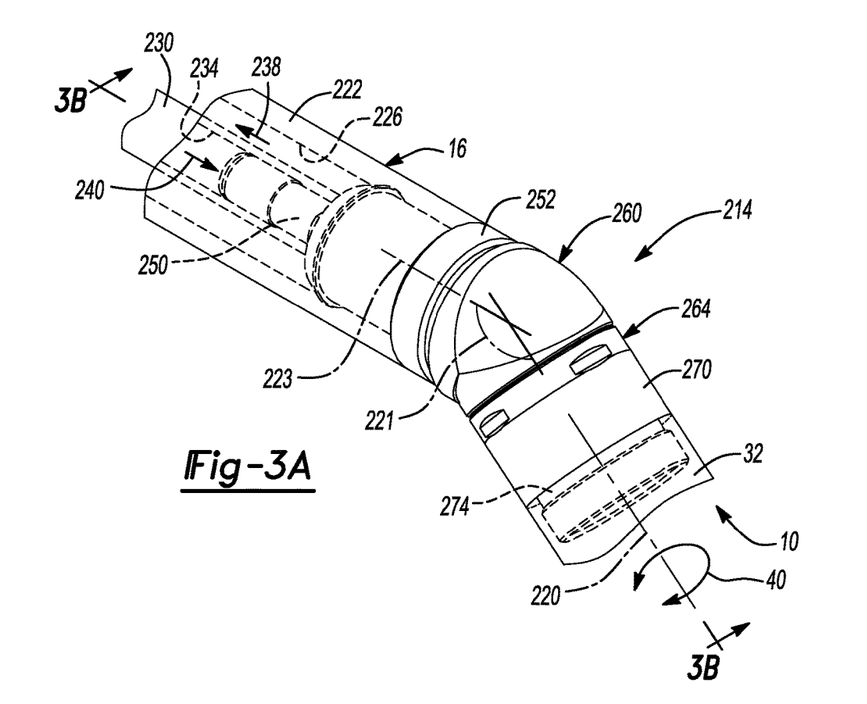
FIG. 3A is an assembled view of a knuckle assembly according to various embodiments.

Turning reference to FIGS. 3A-3E, the knuckle 14 may include, according to various embodiments, a knuckle assembly 214 as illustrated assembled in FIG. 3A. The knuckle 214 may allow the motor assembly 10 to rotate around a first axis 220 in the direction of the double headed arrow 40, as discussed above. The rotation of the housing 32 of the assembly 10 can allow for positioning of the tool 36, as discussed above, while not twisting the supply line 16. The knuckle 214 may be formed to define an angle 221 between the axis 220 and a second axis 223.

The supply line 16, as illustrated in FIG. 3A, can include an outer housing 222 that may have an internal surface 226 and an inner tube 230 having an inner wall surface 234. The supply line assembly 16 allows for venting of the drive fluid between the surfaces 226 and 230 generally in the direction of arrow 238 while a supply pressure drive fluid can be provided through the inner wall 234 of the inner tube 230 generally in direction of arrow 240. The high pressure tube portion 230 of the supply line assembly 16 may be connected to a barb 250 that may be similar or identical to the barb 130 discussed above. The barb 250 will be discussed in further detail herein. The supply line 16 can include a threaded portion 252 that engages or is threaded to a threaded portion 254 of a first portion 260 of the nozzle assembly 214 as discussed above the knuckle 214 further includes a second portion 264 that is interconnected with the housing 32 of the motor assembly 10. The second portion 264 of the knuckle 214 may include two main components or members including a first or outer member 270 and a second or inner member 274.

Figure 3B:
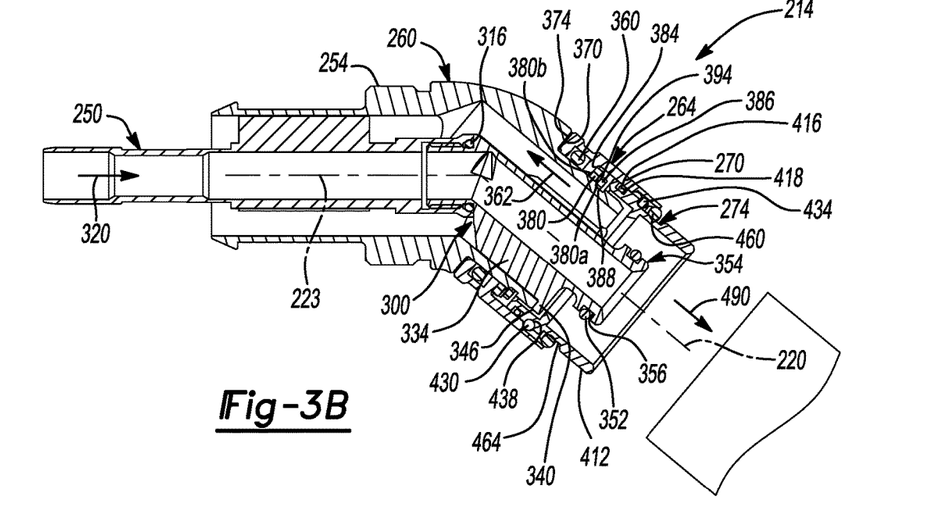
FIG. 3B is a cross sectional view of the knuckle assembly FIG. 3A taken along line 3B.
Figure 3C:
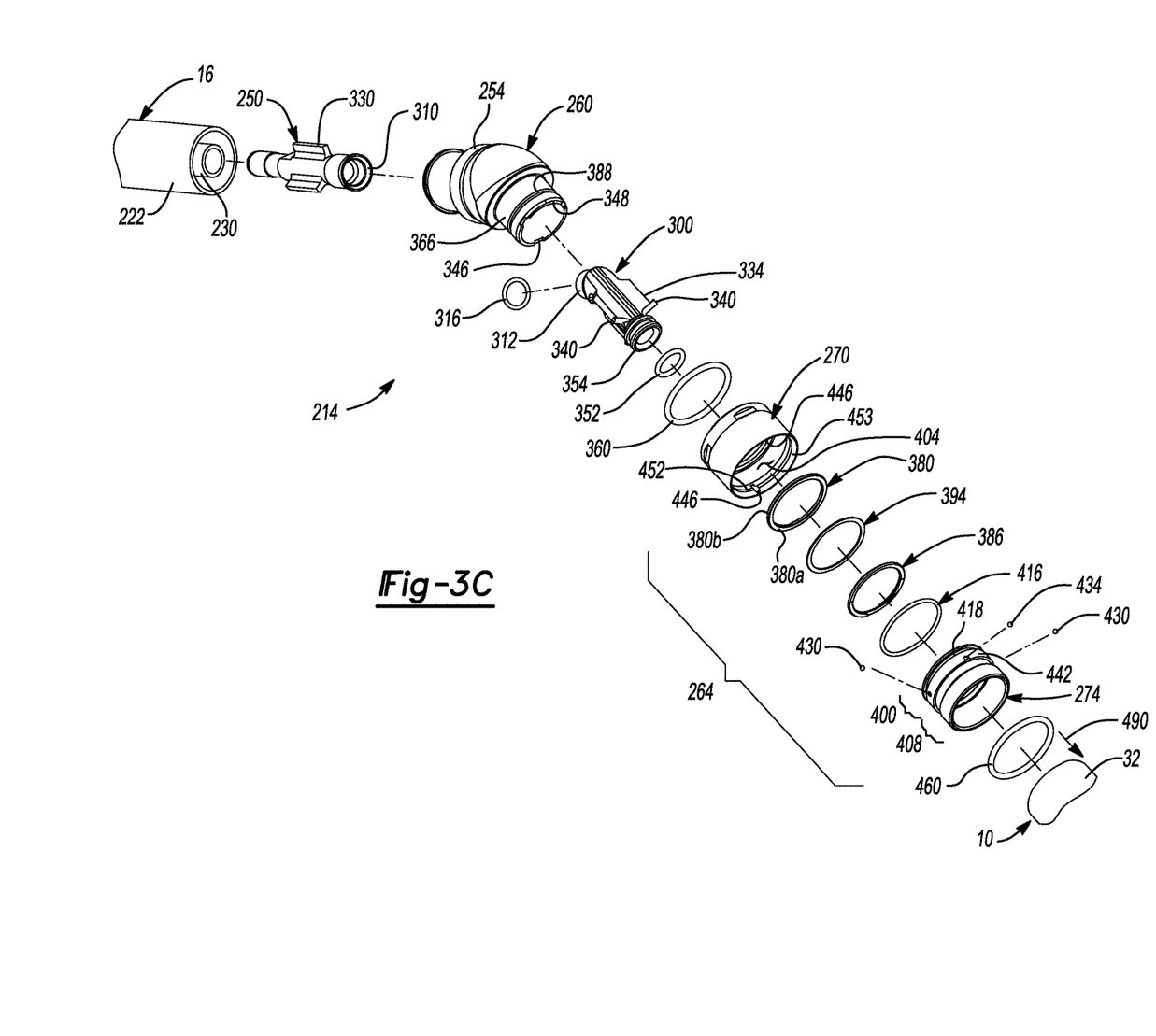
FIG. 3C is an exploded view of the knuckle assembly of FIG. 3A.
Figure 3D:
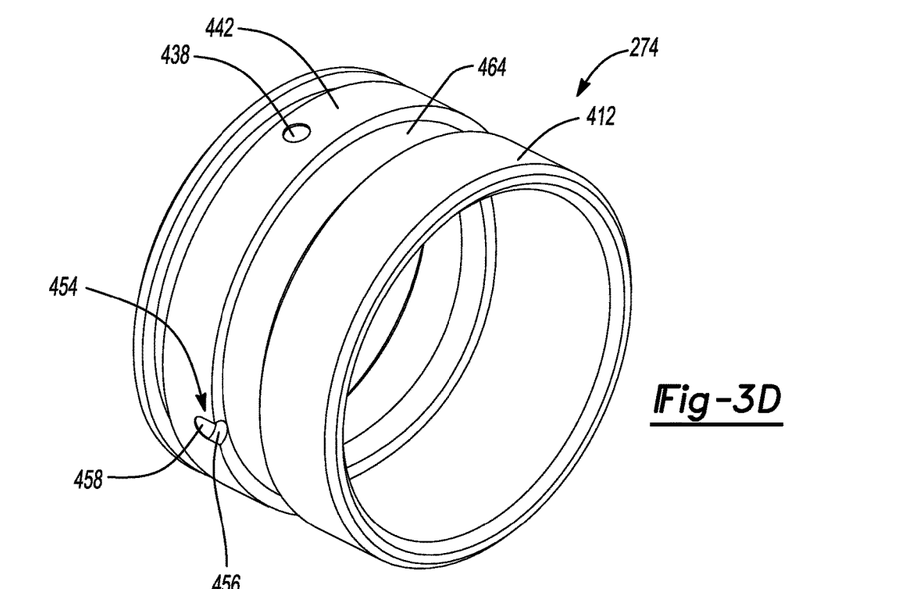
FIG. 3D is a detailed view of a first portion of the knuckle assembly of FIG. 3A.
Figure 3E:
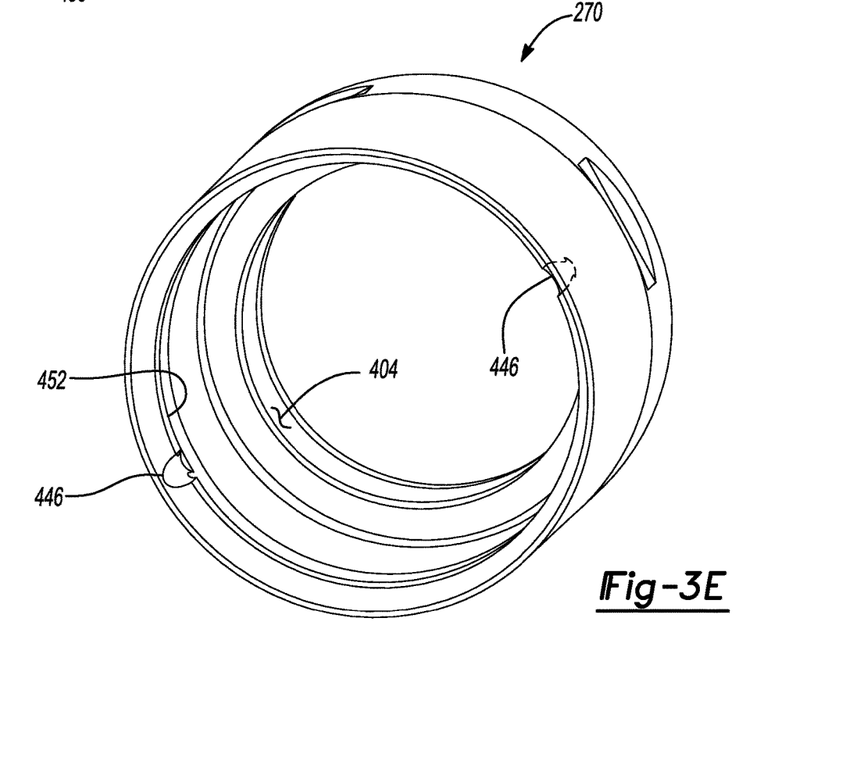
FIG. 3E is a detailed view of a second portion of the knuckle assembly of FIG. 3A.

The knuckle assembly 214 can be assembled, as discussed further herein, to include the portions as illustrated in FIG. 3C and in cross-section in FIG. 3B (taken along line 3B-3B in FIG. 3A). In particular, the barb 250 can be connected with a nozzle 300 in a manner substantially similar to the connection of the barb 130 with the nozzle 136. For example, an internal thread 310 can be formed on the barb 250 and an external thread 312 can be formed on the nozzle 300. It is understood, however, that a connection of the barb 250 with the nozzle 300 can be formed in other manners, such as with a welding, adhesive, or other mechanisms. Similarly, the barb 250 may include projections or other connection portions to fixedly connect with the supply line 16.

A nozzle O-ring 316 may be positioned between the nozzle 300 and the barb 250 prior to connection of the nozzle 300 with the barb 250. As discussed above, a passage through the nozzle 300 and the barb 250 allows for a high pressure flow to drive the motor 30. Therefore, the O-ring 316 can assist in sealing this high pressure flow passage. The high pressure flow can flow through the passage generally in the direction of arrow 320 towards the motor assembly 10. The barb 250 can include positioning or holding fins 330 similar to the fins 132 with the barb 130. Similarly, the nozzle 300 can include positioning or holding fins 334 similar to the fins 146 of the nozzle 136. The respective fins 330, 334 can assist in transverse fixation of the respective barb 250 and nozzle 300 within the knuckle 214. In addition, the nozzle 300 may include one or more tabs or fingers 340 that extend or protrude from the fins 334 or other appropriate portion of the nozzle 300, as discussed further herein. The tabs 340 engage respective notches or indent 346 formed in a distal end 348 of the second portion 260. The interaction of the tabs 340 with the notches 346 reduce or eliminate a rotation of the nozzle 300 within the knuckle assembly 214. Also due to the connection of the nozzle 300 with the barb 250, rotation of the barb 250 is also reduced or eliminated. A second nozzle O-ring 352 may also be connected with a distal end or second end 354 of the nozzle 300, such as in a groove 356 formed on the nozzle 300. The second O-ring 352 can assist in sealing the passageway for the high pressure flow 320 to the motor housing assembly 10.

The second portion 264 of the knuckle assembly 214 includes a plurality of components including the first member 270 and the second member 274. The first member 270 can be sealed relative to the first portion 260 with a first knuckle sealing O-ring 360. The first knuckle sealing O-ring 360 can assist in sealing the exhaust flow path 362 from the motor assembly 10 out of the knuckle 214. The second portion 264 may rotate relative to the first portion 260 in a manner similar to the first portion 116 that can rotate relative to the second portion 118 of the knuckle assembly 114, as discussed above. Due to the moveable connection where the first portion 260 is not fixed to the second portion 264, the knuckle sealing O-ring 360 assists in ensuring a seal of a fluid passage through the knuckle 214.

As illustrated in FIG. 3B, the first member 270 of the second portion 216 may only slightly engage or not engage an outer surface 366 of a distal end of the first portion 260. Further, a transverse end wall 370 of the first member 270 may be spaced apart from an end wall 374 of the first portion 260. The space can allow for ease of rotation of the second portion 264 relative to the first portion 260 of the knuckle assembly 214. Further, a bearing member 380 may be provided to contact the outer surface 316 of the first portion 216 and an internal wall 384 of the first member 270. The internal wall 384 may be a wall that extends transverse to a long axis of a portion of the first portion 260, such as the axis 220. The bearing member 380 may further include end walls 380a and 380b to bear on walls in an axial direction or when force is applied on the bearing member parallel or generally parallel to the axis 220. It is understood, however, that the bearing member 380 may also operate as a bearing feature when force is applied transverse (e.g. perpendicular) to the axis 220 and on a radial surface of the bearing member 380.

The bearing member 380 can be formed or provided as a single annular member that fits around or is positioned around the surface 366 of the first portion 260. The bearing member 380 can be formed of a material substantially similar or identical to the bearing members 170, 184 of the knuckle assembly 114. For example, the bearing member 380 may be formed of tetrafluoroethylene or polytetrafluoroethylene, such as Teflon® PTFE. It is understood, however, that the bearing member 380 may be formed of other materials, such as other polymers or non-polymer materials. For example, the bearing member 380 may also be formed of PEEK (polyetheretherketone).

The bearing member 380 allows for a low coefficient or friction between the second portion 264 and the first portion 260, and particularly between the first member 270 and the surface 366 of the first portion 260 during rotation of the knuckle assembly. The rotation or movement of the first member 270, therefore, may have an ease of movement and smoothness of movement during rotation of the second portion 264 relative to the first portion 260 of the knuckle assembly 214.

The bearing member 380 may be held in place relative to the first member 270 and/or the first portion 260. The bearing member 380 may be held in place with a locking member or ring 386, the locking member 386 may also be referred to as a snap or split ring 386. The snap ring 386 may form a substantially angular ring that may expand as it passes over the distal end 348 of the first portion 260 and then may collapse to engage a groove 388 formed in the surface 366 of the first portion 260. The snap ring 386 can assist in holding the bearing member 380 in a selected position in the knuckle assembly 214. The snap ring 386, therefore, forms a wall or surface that is transverse to the axis 220. As discussed herein, the bearing member 380 may, therefore, bear against the wall 384 and the snap ring 386, even if indirectly as discussed herein.

The snap ring 386, in the embodiment illustrated in FIG. 3C, does not include a substantially smooth external surface due to the expansion feature of the snap ring 386. A non-smooth edge may gauge or damage the bearing member 380 if the bearing member 380 is formed of a material softer than that of the snap ring 386. Therefore, an intermediate member 394 may be positioned between the snap ring 386 and the bearing member 380. The intermediate member 394 may be formed with a smooth external surface and of a harder material than the bearing member 380, such as stainless steel, cobalt chromium alloy, or other appropriate alloys. Generally, the material of the intermediate member 394 and the snap ring 386 may have similar or equal hardness. The bearing member 380 may therefore be held in place in the knuckle assembly 214 by the snap ring 386 due to the positioning of the intermediate member 394.

Accordingly, as discussed above, rotation of the second portion 264 relative to the first portion 260 can have reduced friction between the two members or other interactions reduced due to the interposition of the bearing 380 between the first member 270 and the first portion 260. The assembly of the bearing member 380, the snap ring 386, and the intermediate member 394 can be further positioned or held in place with the second member 274. The second member 274 can include a first section 400 that can extend within or be received in an internal area 404 of the first member 270. A second section 408 of the second member 274 may extend from the first member 270 and allow for an engagement with the housing 32. For example, the second section 408 of the second member 274 may include an external thread 412 that can be engaged with an internal thread of the housing 32 to hold or mount the motor assembly 10 to the knuckle 214. It is further understood that the motor assembly 10 may include connections to engage the distal end 354 of the nozzle 300 to allow for the supply of the high pressure fluid to the motor 30.

A second knuckle sealing O-ring 416 may be positioned in a groove 418 formed in a proximal end of the second member 274. Again, as illustrated in FIG. 3B, the second knuckle O-ring 416 can assist in sealing a passage for the exhaust fluid flow through the passage in flow direction 362.

The second member 274 can be connected to the first member 270, in a process as discussed further herein, with a connection mechanism including three connection or locking members. The connection members may include ball bearings including two axial fixation ball bearings 430 and one rotational fixation locking ball bearing 434. The locking members 430 and 434 may be any appropriate member and may include spherical individual locking members, as discussed and illustrated herein. It is understood that the locking members 430, 434 can be formed of appropriate materials such as being formed as stainless steel ball bearings. Other appropriate materials may include polymer materials, particularly dense or rigid polymer materials, that may assist in holding or fixing the first member 270 relative to the second member 274.

The axial fixation locking members 430 may be positioned in locking pockets 438 that are formed as indents in an external surface 442 of the second member 274. Once the locking members 430 are positioned in the indents 438, the locking members are held in a selected position relative to the second member 274. Further, the locking members 430 once held in the pockets 438 may be aligned with respective grooves 446 formed in an internal surface 453 of the first member 270. The first member 270 may then be rotated relative to the second member 274 to move the locking members 430 into an internal groove 452, which may be formed as substantially annular groove, formed in the internal surface 453 of the first member 270.

The rotational locking member 434 may be positioned in a rotational locking groove 454 that has an opening 456 at a first end and is closed at a second end wall 458. As discussed herein, the rotational locking member 434 can be positioned in the rotational locking groove 454 formed in the second member 274. A holding or locking mechanism O-ring member 460 may be positioned in a locking member groove 464 formed in an external surface of the second member 274. The housing 32 of the motor assembly 10, when threaded on the external thread 412, may assist in holding the locking O-ring member 460 in place. The locking O-ring 460 may be similar to a sealing O-ring or may be formed with other elastic material to allow it to be passed over the threads 412 and engage within the groove 464 to assist in holding the rotational locking member 434 within the locking groove 454.

Accordingly, when assembled, the knuckle assembly 214 allows for rotation of the second portion 264 relative to the first portion 260. The bearing member 380 bearing against the internal wall 384 can assist in bearing and allowing rotation of the second portion 264 relative to the first portion 260 in addition to achieving a selected coefficient of friction between the second portion 264 and the first portion 260. Generally, the motor housing affixed to the threads 412 of the second member 274 may pull or include a bias generally in the direction of arrow 490, as illustrated in FIGS. 3B and 3C. As the motor assembly 10 is moved in the direction of arrow 490, the internal surface 384 bears against and contacts the bearing member 380. Therefore, the bearing member 380 then engages the intermediate member 394 and then locking ring 386. The bearing member 380, therefore, provides a bearing contact between the internal wall 384 and the locking snap ring 386 (via the intermediate member 394), which holds the bearing member 380 relative to the first portion 260.

In assembling the knuckle assembly 214, the first member 270 is rotationally and axially fixed relative to the second member 274 with the locking members 430 and 434. The assembly process is illustrated in FIGS. 4A-4D. With initial reference to FIG. 4A the assembly of the first member 270 to the second member 274 may occur after the first member 274 is connected to the first portion 260. Further, the bearing member 380, intermediate member 394, and the snap ring 386 may also be assembled to the first portion, as discussed above. Accordingly connection of the second member 274 to the first member 270 may be near the end of the assembly of the knuckle assembly 214. Further, the proper connection of the first member 270 and the second member 274 may ensure and/or correct proper placement of the snap ring 386 and the related bearing member 380 and the intermediate member 394.

Figure 4A:
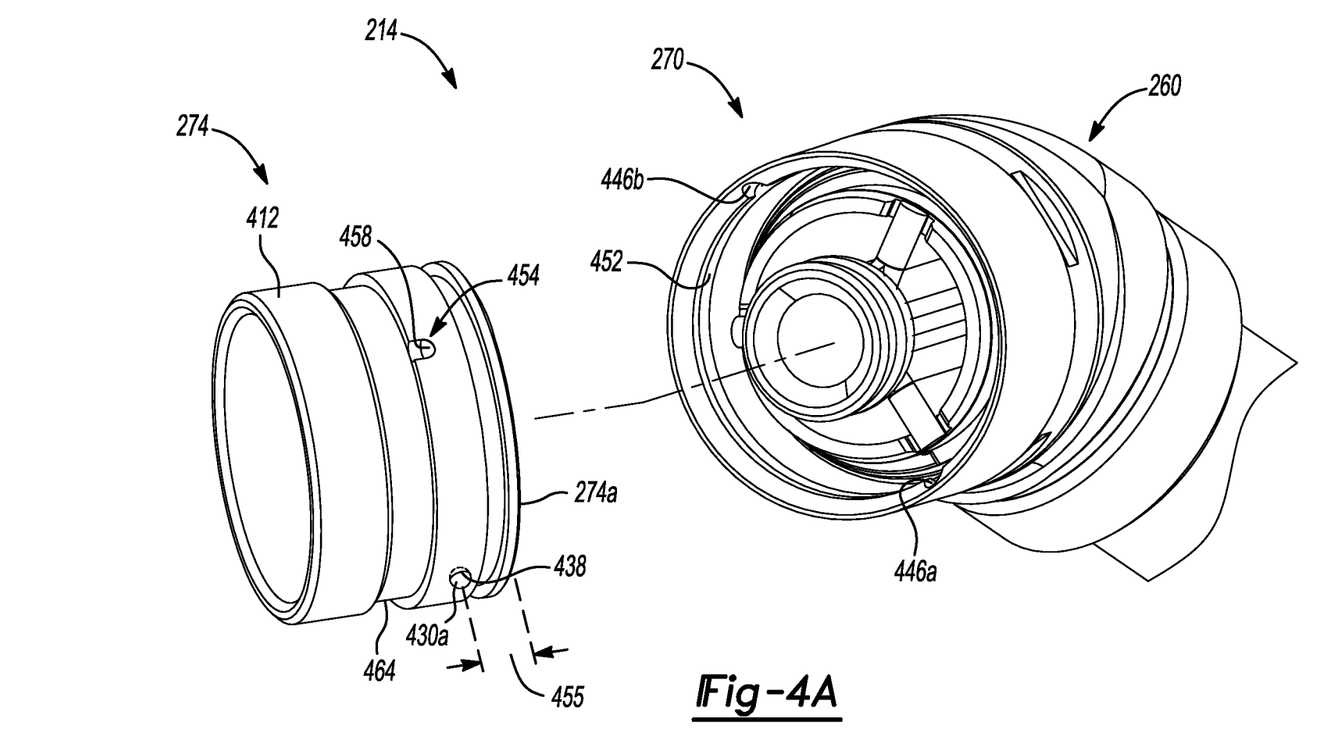
FIG. 4A-4D is an illustration of an assembly of the second portion of the knuckle assembly illustrated in FIG. 3A.
Figures 4B, 4C, 4D:
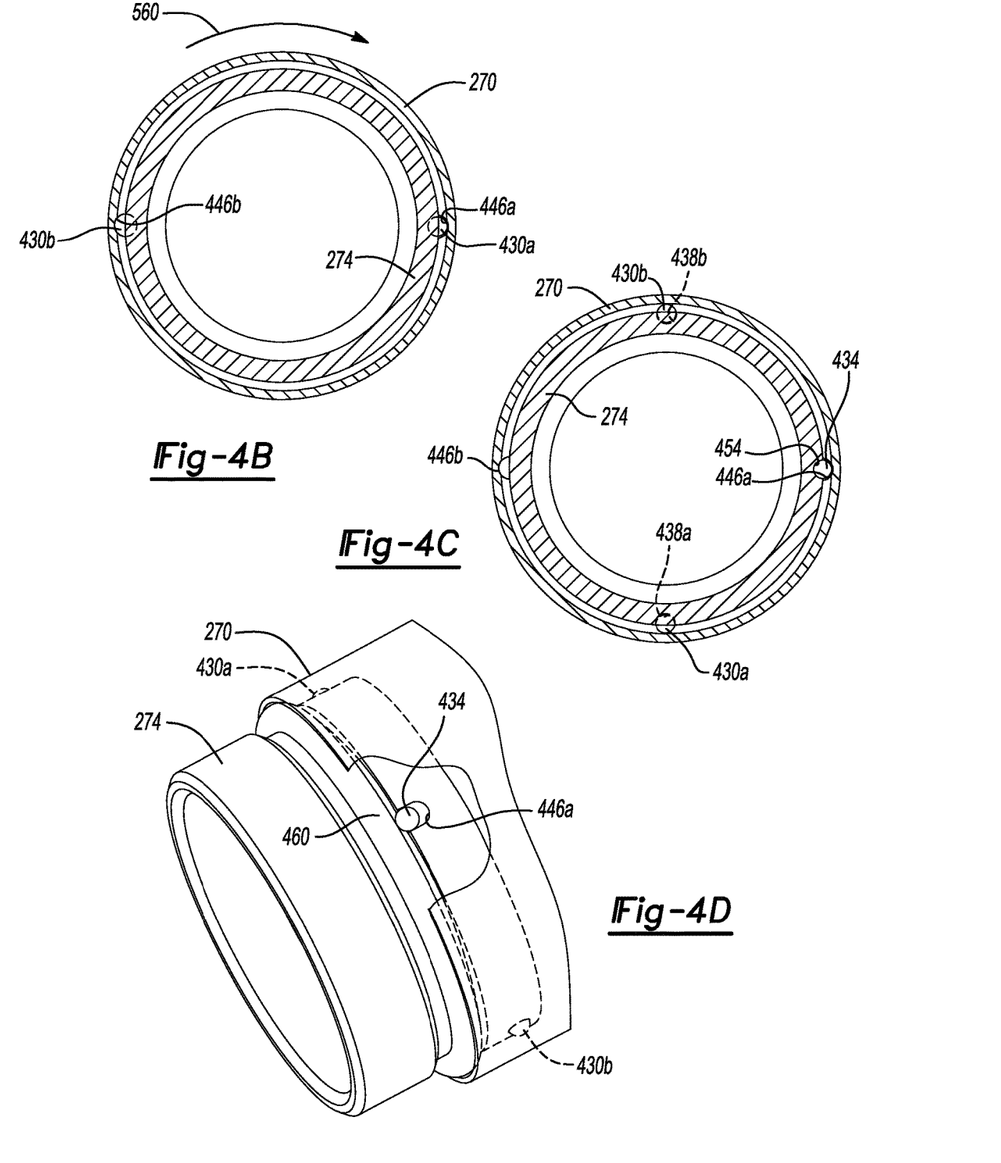

As illustrated in FIG. 4A a first step may include axially positioning the axial locking member 430 in the pocket 438 and rotationally aligning the axial locking member 430 with one of the grooves 446. Similarly, another of the locking member 430 may be positioned in the second pocket 438b which may 180 degrees spaced apart from the pocket 438a, as illustrated in FIG. 4B. Therefore the second axial locking member 430 may be rotationally aligned with one of the grooves 446 to allow the second member 274 to be axially inserted into the first member 270.

Turning reference to FIG. 4B, once the second member 274 is pushed into or moved axially into the first member 274, the first and second locking members 430a and 430b are received in the first and second grooves 446a and 446b, respectively. The second member 274 may then be rotated substantially 90 degrees relative to the first member 270, such as generally in the direction of arrow 560. The second member 274 may be rotated relative to the first member 270 as the locking members 430a, 430b have been moved into the groove 452 formed within the first member 270. The groove 452 is substantially an annular groove that extends around the entire internal circumference of the first member 270. Therefore, the second member 274 may be rotated relative to the first member 270 a selected amount. The rotation of 90 degrees is selected due to positioning of the rotational locking groove 454. It is understood that any other appropriate rotational amount can be selected based upon a position of the rotational locking group 454.

As discussed above, when selectively and properly installed, the snap ring 386 may form a substantially angular ring that may expand as it passes over the distal end 348 of the first portion 260 and then may collapse to engage the groove 388 formed in the surface 366 of the first portion 260. The snap ring 386 can assist in holding the bearing member 380 in the selected position in the knuckle assembly 214. With reference to FIGS. 4A and 4B, a distance 455 between pockets 438 and/or the locking member 430 and an end 274a of the second member 274 may be selected so that the end 274a extends into the first member 270, when the locking members are able to move in the internal groove 452, such that the end 274a is adjacent or flush with the groove 388 in the first portion 260. The distance 455 may ensure that the snap ring 386 is properly seated in the groove 388. If the snap ring 386 is not properly seated, the end 274a will push the snap ring 386 into the groove 388 before the locking members 430 may move in the groove 452 and allow the first member 270 to rotate relative to the second member 272. Thus, the connection of the first member 270 and the second member 272 may assist to ensure proper placement and connection of the snap ring 386 and the bearing member 380.

Turning reference to FIG. 4C, the locking members 430a and 430b are axially constrained within the groove 452 in the first member 270 and the respective pockets 438a and 438a in the second member 274 once the second member 274 is axially slid into the first member 270. This may also ensure, as discussed above, that the bearing member 380, intermediate member 394, and the snap ring 386 are also properly installed and seated. Due to the rotation of the second member 274 relative to the first member 270, the rotational locking pocket 454 is aligned with the groove 446a. It is understood, however, that the rotational locking groove 454 can also be aligned with the groove 446b by rotating the second member 274 relative to the first member 270 in a direction opposite that illustrated in FIG. 4C.

Due to the alignment of the rotational locking groove 454 with the groove 446a, the rotational locking member 434 can be positioned into a passage formed by the rotational locking groove 454 and the groove 446a. in various assembly embodiments, the rotational locking member 434 may be dropped or slid into the passage. The rotational locking member 434 may, also, be precisely placed in the passage with the robotic system, fine manipulators (e.g. tweezers), or other appropriate placement system.

The rotational locking member 434 is held within the rotational locking pocket 454 by the back terminal wall 458 at a distance that is away from the angular internal groove 452 of the first member 270. Therefore, the rotational locking member 434 does not enter the groove 452 and cannot move within the groove 452. Once the rotational locking member 434 is positioned within the rotational locking pocket 454, the second member 274 may no longer rotate relative to the first member 270. A locking member, such as the locking O-ring 460 can be positioned in the locking groove 464 to ensure that the rotational locking member 434 remains within the rotational locking pocket 454.

The connection mechanism, including the locking members 430 and 434 and the pockets 438 and 454 and the grooves 446 allow the second member 274 to be axially locked or fixed (such that it cannot be pulled away from the first member 270) and rotationally locked or fixed (such that it does not rotate relative to the first member 270). Accordingly, when the motor assembly 10 is connected to the external threads 412 of the second member 274, the motor assembly 10 will rotate both the second member 274 and the first member 270 relative to the first portion 260. The two members 270, 274 are connected due to the connection mechanism including the locking members 430 and 434. The two members 270 and 274, therefore, may move as one once connected. The bearing member 380 will bear the rotation of the second portion 264 relative to the first portion 260.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A swivel connection assembly between a power supply and a surgical motor assembly, comprising:
   a first portion having a first section extending along a first longitudinal axis and a second section extending along a second longitudinal axis, wherein the first axis and the second axis are at a non-zero angle relative to one another;
   a first annular wall radially extending from an exterior surface of the second section transverse toward the second axis to define a first exterior annular wall surface;
   a second portion extending along a third axis;
   a second annular wall radially extending towards the third axis from an internal surface of the second portion to define a second internal annular wall surface;
   a single piece annular bearing member having a first annular end surface and a second annular end surface and positioned between the first annular wall and the second annular wall;
   a separate barb having an external barb wall extending from a first end to a second end and forming a barb passage through the barb; and
   a separate nozzle having an external nozzle wall extending from a third end to a fourth end and forming a nozzle passage through the nozzle;
   wherein the first annular end surface engages the first exterior annular wall surface and the second annular end surface engages the second internal annular wall surface;
   wherein the first portion and the second portion both bear on the annular bearing member and are rotatable relative to one another;
   wherein the barb and the nozzle are fixedly connected directly together to form a high pressure flow path from a supply to a motor and positioned within the first and second portions.

2. The swivel connection assembly of claim 1, wherein the annular bearing member is molded as a single piece to form continuous first and second annular end surfaces.

3. The swivel connection assembly of claim 1, wherein the annular bearing member is formed as a single piece from at least one of polyetheretherketone or polytetrafluoroethylene.

4. The swivel connection assembly of claim 1, wherein the bearing member bears contact in a direction substantially parallel with the second axis.

5. A swivel connection assembly between a power supply and a surgical motor assembly, comprising:
   a first portion having a first section extending along a first longitudinal axis and a second section extending along a second longitudinal axis, wherein the first axis and the second axis are at a non-zero angle relative to one another;
   a first annular wall radially extending from an exterior surface of the second section transverse toward the second axis to define a first exterior annular wall surface;
   a second portion extending along a third axis;
   a second annular wall radially extending towards the third axis from an internal surface of the second portion to define a second internal annular wall surface;
   a single piece annular bearing member having a first annular end surface and a second annular end surface and positioned between the first annular wall and the second annular wall;

wherein the first annular end surface engages the first exterior annular wall surface and the second annular end surface engages the second internal annular wall surface;

wherein the first annular end surface engages the first exterior annular wall surface and the second annular end surface engages the second internal annular wall surface;

wherein the first portion and the second portion both bear on the annular bearing member and are rotatable relative to one another;

wherein the first section of the first portion includes an external thread to threadably connect to a supply tube.

6. The swivel connection assembly of claim 5, wherein the second portion includes an external threaded portion at a distal end of the second portion to threadably engage the surgical motor assembly.

7. A swivel connection assembly between a power supply and a surgical motor assembly, comprising:
   a first portion having a first section extending along a first longitudinal axis and a second section extending along a second longitudinal axis, wherein the first axis extends relative to the second axis;
   a first exterior annular surface extending radially from an exterior surface of the second section transverse toward the second axis;
   a second portion extending along a third axis;
   a second internal annular surface extending radially towards the third axis from an internal surface of the second portion;
   a single piece annular bearing member having a first annular end surface and a second annular end surface and positioned between the first exterior annular surface and the second internal annular surface;
   a snap ring configured to surround the exterior surface of the second section; and
   an annular groove formed into the exterior surface of the second section;
   wherein the first annular end surface engages the first exterior annular surface and the second annular end surface engages the second internal annular surface;
   wherein the first portion and the second portion both bear on the annular bearing member and are rotatable relative to one another;
   wherein the snap ring fits into the annular groove;
   wherein the snap ring forms at least a portion of the first annular surface that engages the first annular end surface of the annular bearing member.

8. The swivel connection assembly of claim 7, further comprising:
   an intermediate ring positioned between the bearing member and the snap ring;
   wherein the intermediate ring forms at least a portion of the first annular surface that engages the first annular end surface of the annular bearing member;
   wherein the bearing member directly contacts the intermediate ring.

9. The swivel connection assembly of claim 8, wherein both the snap ring and the intermediate ring are removable from the first portion.

10. The swivel connection assembly of claim 7, wherein the second portion includes a first member extending along the third axis and a second member extending along the third axis.

11. The swivel connection assembly of claim 10, wherein the first member forms the second annular surface.

12. The swivel connection assembly of claim 10, further comprising:
   a connection mechanism configured to selectively rotationally and axially fix the first member and the second member.

13. A method of forming a swivel connection assembly between a power supply and a surgical motor assembly, comprising:
   forming a first portion having a first section extending along a first longitudinal axis and a second section extending along a second longitudinal axis, wherein the first axis extends relative to the second axis;
   installing the first portion to include a first exterior annular surface extending radially from an exterior surface of the second section transverse toward the second axis;
   forming a second portion extending along a third axis;
   forming a second internal annular surface extending radially towards the third axis from an internal surface of the second portion;
   installing a single piece annular bearing member having a first annular end surface and a second annular end surface and positioned between the first exterior annular surface and the second internal annular surface;
   expanding an annular ring member over the exterior surface of the second section;
   moving the annular ring to a groove formed in the exterior surface; and
   allowing the annular ring to fit into the groove;
   wherein the first annular end surface engages the first exterior annular surface and the second annular end surface engages the second internal annular surface;
   wherein the first portion and the second portion both bear on the annular bearing member and are rotatable relative to one another.

14. The method of claim 13, wherein installing the single piece annular bearing member includes moving the single piece annular bearing member past the groove along the second axis.

15. The method of claim 14, further comprising:
   installing a separate intermediate member after installing the single piece bearing member;
   wherein the intermediate member is positioned between the single piece bearing member and the annular ring member.

16. The method of claim 13, further comprising:
   installing a separate intermediate member between the single piece bearing member and the annular ring member.

* * * * *